United States Patent [19]

Wu

[11] Patent Number: 5,162,595
[45] Date of Patent: Nov. 10, 1992

[54] ETHYLENE DIMERIZATION
[75] Inventor: An-hsiang Wu, Bartlesville, Okla.
[73] Assignee: Phillips Petroleum Company, Bartlesville, Okla.
[21] Appl. No.: 809,776
[22] Filed: Dec. 18, 1991
[51] Int. Cl.$^5$ .............................................. C07C 2/24
[52] U.S. Cl. ..................... 585/513; 585/510; 585/511; 585/512; 585/514; 585/520; 585/527
[58] Field of Search ............... 585/510, 511, 512, 513, 585/514, 520, 527

[56] References Cited

U.S. PATENT DOCUMENTS

| | | | |
|---|---|---|---|
| 3,414,629 | 12/1968 | McCall et al. | 260/666 |
| 3,452,115 | 6/1969 | Schneider | 260/683.15 |
| 3,513,218 | 5/1970 | Galtings et al. | 260/683.15 |
| 3,642,935 | 2/1972 | Dunning et al. | 585/513 |
| 3,697,617 | 10/1972 | Yoo et al. | 585/513 |
| 3,755,490 | 8/1973 | Yoo et al. | 585/513 |
| 3,992,323 | 11/1976 | Yoo et al. | 252/430 |
| 4,155,946 | 5/1979 | Sato et al. | 585/513 |
| 4,387,262 | 6/1983 | Chauvin et al. | 585/512 |
| 4,482,640 | 11/1984 | Knudsen et al. | 502/155 |
| 4,487,847 | 12/1984 | Knudsen | 502/155 |
| 4,518,814 | 5/1985 | Knudsen et al. | 585/523 |
| 4,528,415 | 7/1985 | Knudsen | 585/527 |
| 4,992,610 | 2/1991 | Sato et al. | 585/512 |

Primary Examiner—Patrick P. Garvin
Assistant Examiner—E. D. Irzinski
Attorney, Agent, or Firm—William R. Sharp

[57] ABSTRACT

An ethylene dimerization process is provided wherein ethylene is contacted with an organonickel(II) compound, a phosphite compound and an alkylaluminum compound in a solvent to produce a precursor reaction mixture, followed by contacting ethylene with the precursor reaction mixture and a fluorinated organoacid to produce a product reaction mixture comprising a $C_4$ fraction of predominantly 2-butenes.

16 Claims, No Drawings

ETHYLENE DIMERIZATION

This invention relates to a process for dimerizing ethylene to butenes, comprising predominantly 2-butenes.

2-butenes are useful in metathesis processes to produce other olefins such as propylene, and are also useful in alkylation processes in the production of motor fuels. It would be desirable to provide a process of dimerizing ethylene to butenes which achieves a combination of high productivity and high selectivity to 2-butenes.

It is, therefore, an object of the invention to provide an improved process for dimerizing ethylene which achieves the above-mentioned desired combination of results.

The above object is achieved by a process for dimerizing ethylene to butenes, comprising the steps of: (a) contacting ethylene, an organonickel(II) compound (having nickel in a valence state of +2), a phosphite compound of the formula $P(OR)_3$ where R independently represents H or a $C_1$ to $C_{20}$ hydrocarbyl radical and where at least one R is not H, and an alkylaluminum compound having at least one $C_1$ to $C_{12}$ alkyl radical and at least one aluminum atom per molecule, wherein the ethylene is in a gaseous phase and the organonickel(II) compound, phosphite compound and alkylaluminum compound are in a first solvent and in a liquid phase, thereby producing a precursor reaction mixture in a liquid phase; and (b) contacting, after step (a), ethylene in a gaseous phase, the precursor reaction mixture, and a fluorinated organoacid in a liquid phase, thereby producing a product reaction mixture in a liquid phase comprising the desired butenes. The fluorinated organoacid in step (b) can, if desired, be in a second solvent.

Suitable organonickel(II) compounds include bis(cyclopentadienyl) nickel(II), bis(pentamethylcyclopentadienyl) nickel(II), nickel(II) 2-ethylhexanoate, nickel(II) acetylacetonate, nickel(II) trifluoracetylacetonate, nickel(II) hexafluoroacetylacetonate, nickel(II) acetate, nickel(II) hydroxyacetate, nickel(II) stearate, nickel(II) cyclohexanebutylrate and nickel(II) oxalate. The first six listed organonickel(II) compounds, particularly nickel(II) acetylacetonate, are preferred. Each of such preferred organonickel(II) compounds have a nickel atom bonded to at least one organic ligand by means of a main valence bond and a coordination bond. In addition, a hydrated form of the organonickel(II) compound is preferred as being less expensive and more stable than the anhydrous form of such compound, although the anhydrous form can be employed if desired.

Suitable phosphite compounds of the formula $P(OR)_3$, where R independently represents H or a $C_1$ to $C_{20}$ hydrocarbyl radical and where at least one R is not H, include di-n-butylphosphite, diethylphosphite, diisopropylphosphite, tri-n-butylphosphite, triethylphosphite, trimethylphosphite, tri-neo-pentylphosphite, triphenylphosphite, triisopropylphosphite, tricyclohexylphosphite and tris(ortho-tolyl)phosphite. Tris(ortho-tolyl)phosphite is preferred as optimizing productivity.

Suitable alkylaluminum compounds having at least one $C_1$ to $C_{12}$, preferably $C_1$ to $C_6$, alkyl radical and at least one aluminum atom per molecule include triisobutylaluminum, triethylaluminum, trimethylaluminum, di-isobutylaluminum chloride, di-isobutylaluminum hydride, diethylaluminum chloride and triethyldialuminum trichloride. Particularly preferred in accordance with the invention is a trialkylaluminum compound of the formula $AlR'_3$ where R' is the above-mentioned alkyl radical, such as triisobutylaluminum, triethylaluminum or trimethylaluminum, Triethylaluminum is most preferred.

The preferred fluorinated organoacid is a fluorinated carboxylic acid of the formula $R''COOH$ where $R''$ represents a $C_1$ to $C_{10}$ hydrocarbyl radical having at least one fluorine (F) atom. Suitable fluorinated carboxylic acids include trifluoroacetic acid, heptaflurobutyric acid, difluoroacetic acid, pentafluoropropionic acid and perfluoroadipic acid. The preferred fluorinated carboxylic acid is trifluoroacetic acid. Fluorinated organoacids also within the scope of certain broad aspects of the invention are fluorinated sulfonic acids such as trifluoromethanesulfonic acid and heptafluoroethanesulfonic acid.

The preferred molar ratio of (i) the phosphite compound, (ii) the alkylaluminum compound, and (iii) the fluorinated organoacid, respectively, to the organonickel(II) compound are as follows: (i) about 0.1-5 to 1, most preferably about 0.8-1.2 to 1; (ii) about 1-10 to 1, most preferably about 1.5-2.5 to 1; and (iii) about 1-20 to 1, most preferably about 5-7 to 1.

The first solvent, as recited in step (a) above, is selected from the group consisting of: a saturated hydrocarbon or fluorinated hydrocarbon of the formula $C_nH_{2n+2-x}F_x$ where $n=4, 5, 6, 7$ or $8$ and $x=0, 1$ or $2$; and an aromatic hydrocarbon or fluorinated hydrocarbon of the formula $C_6H_{6-n}(R''')_n$ where $n=0, 1, 2, 3,$ or $4$ and $R'''$ independently represents F or a $C_1$ to $C_6$ alkyl radical or fluorinated alkyl radical. Suitable saturated hydrocarbons or fluorinated hydrocarbons include isobutane, isopentane, neohexane, n-heptane, n-pentane, n-hexane, octane, isooctane, perfluoralkanes and fluorinated alkanes. Suitable aromatic hydrocarbons or fluorinated hydrocarbons include $\alpha,\alpha,\alpha$-trifluorotoluene, 2-fluorotoluene, 3-fluorotoluene, 4-fluorotoluene, fluorobenzene, difluorobenzene (1,2; 1,3; 1,4), difluorotoluene (2,4; 2,5; 2,6; 3,4), toluene, benzene, ethylbenzene and xylene (o, p, m). The aromatic hydrocarbons are preferred.

The second solvent, which is recited above as being optionally employed in step (b) in conjunction with the fluorinated organoacid, is selected from the group consisting of: a saturated hydrocarbon or fluorinated hydrocarbon as described above; an aromatic hydrocarbon or fluorinated hydrocarbon also as described above; and an alcohol of the formula $(R^{iv})_3COH$ where $R^{iv}$ independently represents H, F or a $C_1$ to $C_{12}$ alkyl, cycloalkyl, aryl, alkaryl, or aralkyl radical and where at least one $R^{iv}$ is neither H nor F. Suitable alcohols include 1-propanol, 1-butanol, 2-methyl-2-butanol (t-amyl alcohol), 1-pentanol, 2-pentanol, 1-hexanol, 1-octanol and 1-decanol.

The weight ratio of the first solvent to the combination of the organonickel(II) compound, phosphite compound and alkylaluminum compound, and also the weight ratio of the second solvent to the fluorinated organoacid, can be in the broad range of about $1-10^6$ to 1, most preferably in the range of about 5-10,000 to 1. The amount of solvent employed depends upon the cost, ease of product recovery therefrom, reactor size, and other practical considerations.

The particular procedure by which the various reagents are contacted as in (a) and (b) above can take a variety of forms.

In accordance with step (a), the organonickel(II) compound, phosphite compound, and alkylaluminum compound in the first solvent and in liquid phase can be contacted with ethylene in gaseous phase in a first vessel by agitating the liquid phase therein and pressuring the first vessel with the ethylene to a predetermined pressure. Most preferably, the organonickel(II) compound, phosphite compound and first solvent are first added to the first vessel, followed by addition of the alkylaluminum compound.

In accordance with step (b), the acid can be added to a second vessel, and either the precursor reaction mixture resulting from step (a) can be transferred from the first vessel to the second vessel or the acid can be transferred to the first vessel. In either case, the precursor reaction mixture and acid are preferably agitated in whichever vessel receives all liquid reagents and such vessel is pressured with ethylene to a predetermined reaction pressure. Most preferably, the acid is contacted with ethylene in the second vessel prior to contacting with the precursor reaction mixture.

The vessel in which step (b) is carried out can be an autoclave or other similar pressure reactor, and the vessel in which step (a) is carried out can be such a reactor or an associated addition vessel, depending on the particular procedure employed.

Pressure and temperature conditions in steps (a) and (b) are such that the ethylene is in a gaseous phase and the organonickel(II) compound, phosphite compound and alkylaluminum compound as in the first solvent and the acid, optionally in the second solvent, are in the liquid phase. More specifically, step (a) is preferably carried out at a pressure of about 5 to 5000 psig and a temperature of about $-100°$ C. to about 50° C., most preferably at a pressure of about 20 to about 1000 psig and a temperature of about 15° C. to about 35° C. (generally ambient temperature conditions). Step (b) is preferably carried out at a pressure of about 5 to about 5000 psig and a temperature of about 0° C. to about 125° C., most preferably at a pressure of about 200 to about 1000 psig and a temperature of about 20° C. to about 50° C.

With respect to time, step (a) is preferably carried out for a time of about 1 minute to about 6 hours, most preferably about 15 minutes to about 3 hours. Step (b) is preferably carried out for a time of about 1 minute to about 15 hours, most preferably about 15 minutes to about 5 hours.

The butenes as contained in the product reaction mixture resulting from step (b) can be separated and recovered from the product reaction mixture by conventional means such as fractional distillation. As demonstrated in examples to follow, such butenes are predominantly (at least about 90 weight percent) 2-butenes.

Many variations of the invention are possible in light of the above teachings. For example, although the invention is described above in terms of a batchwise process, it is within the scope of certain broad aspects of the invention to employ a continuous process wherein ethylene is passed continuously into a reaction zone while product reaction mixture containing the butenes is concomitantly withdrawn therefrom.

Examples are set forth below which further illustrate the invention but which should not be construed to limit the invention in any manner.

Each example employed a 300 mL stainless steel (316SS) Autoclave Engineers stirred tank autoclave, hereafter denoted simply as a reactor. Other equipment employed in individual examples will be referenced in those examples. It is understood that the contents of such reactor in the following examples are being agitated, typically at a slow agitation of about 300 rpm during purging of the reactor or addition of various reagents to the reactor, and at a normal agitation of about 1600 rpm at all other times.

Product analysis was performed on approximately 5 gram samples with an HP 5890 II GC-FID Spectrometer equipped with a capillary DB-1 (60 m) column. The column was operated at 30° C. for 5 minutes, followed by a 15° C./minute increase to 285° C. which was held for 13 minutes. Detection was obtained using a flame ionization detector in the area percent mode. Selectivity and weight percent distribution, discussed further below, were determined from spectra as recorded by the spectrometer.

In the following examples, results are reported in terms of productivity, weight percent $C_4$ and selectivity to 1-butene, trans-2-butene and cis-2-butene. Productivity is defined as the grams of oligomerization product (olefinic oligomers of ethylene, i.e. $C_nH_{2n}$, or simply "$C_n$", where $n=4,6...$) produced per gram of Ni per hour, and was calculated in each example based on grams of ethylene reacted. Weight percent $C_4$ is the weight percent of the dimer $C_4$ of the total oligomerization product. Selectivity to 1-butene, trans-2-butene and cis-2-butene is given in terms of the weight percent of the total $C_4$ fraction.

EXAMPLE I

This example demonstrates dimerization of ethylene in accordance with the invention employing anhydrous nickel(II) acetylacetonate, a variety of different phosphite compounds, triethylaluminum and trifluoroncetic acid.

A reactor was purged with nitrogen for 5 minutes followed by addition of 50 mL of freshly distilled toluene, a phosphite (0.95 mmol) shown in Table I and anhydrous nickel(II) acetylacetonate (0.244 g; 0.95 mmol). 0.5 mL of a 1.9M solution of triethylaluminum (0.95 mmol) in toluene was then added through an addition valve of the reactor. The reactor was then sealed, purged with ethylene six times, and then pressured to 200 psig with ethylene for 30 minutes. All of the above described steps were undertaken at ambient temperature (about 25° C.).

Freshly distilled trifluoroacetic acid (0.325 g; 2.85 mmol) was added to a 40 mL addition vessel equipped with a pressure gauge, by the use of a syringe. The vessel was immediately sealed and pressured to 700 psig with ethylene. The contents of the addition vessel, including the ethylene, were then transferred to the reactor at the end of the above-mentioned 30 minute period through its addition valve. Reaction proceeded immediately, evidenced by the rise in reaction temperature. The reaction temperature was controlled at the temperature (Rx Temp. in °C.) indicated in Table I by use of external cooling water. The internal reactor pressure was maintained at 700 psig and the reaction was continued for a time (Rx time in minutes) also indicated in Table I.

At the end of the reaction period, a sample of the product reaction mixture was taken from the reactor through its sample valve into a 50 mL pressure sample tube, and was analyzed as described above. The resulting selectivities and weight percent $C_4$ data, along with corresponding phosphite compound and productivity, are set forth in Table I.

TABLE I

| Run | Phosphite | Rx Temp. | Rx Time | Productivity | Wt. % $C_4$ | Selectivity wt. % 1-, trans-2-, cis-2-butene |
| --- | --- | --- | --- | --- | --- | --- |
| 1 | Trimethylphosphite | 40 | 60 | 817 | 94 | 10,66,24 |
| 2 | Triethylphosphite | 40 | 60 | 881 | 94 | 10,65,25 |
| 3 | Triisopropylphosphite | 40 | 30 | 982 | 96 | 7,64,29 |
| 4 | Tri-n-butylphosphite | 40 | 30 | 1558 | 95 | 10,63,27 |
| 5 | Triphenylphosphite | 39 | 60 | 1864 | 95 | 8,67,25 |
| 6 | Tris(ortho-tolyl)phosphite | 40 | 30 | 3779 | 94 | 10,61,29 |
| 7 | Tricyclohexylphosphite | 38 | 60 | 525 | 95 | 9,63,28 |

The results of Table I indicate a weight percent of $C_4$ of the total oligomerization product to be at least 94 weight percent, with the selectivity to 2-butenes being at least 90%. Table I also indicates a productivity as high as 3779 g/g/hr with tris(ortho-tolyl)phosphite as the phosphite compound.

EXAMPLE II

This example further demonstrates ethylene dimerization in additional runs which are similar to the runs of Example I except for the below noted differences.

The runs of this example were carried out similarly to the runs of Example I except for the following: hydrated nickel(II) acetylacetonate (0.278 g; 0.95 mmol) was used instead of anhydrous nickel(II) acetylacetonate; 1 mL of the 1.9M triethylaluminum solution was employed instead of 0.5 mL; and a greater amount (0.650 g; 5.70 mmol) of trifluoroacetic acid was used. Reaction times, reaction temperatures, and butene product data are provided in Table II.

TABLE II

| Run | Phosphite | Rx Temp. | Rx Time | Productivity | Wt. % $C_4$ | Selectivity wt. % 1-, trans-2-, cis-2-butene |
| --- | --- | --- | --- | --- | --- | --- |
| 8 | Trimethylphosphite | 40 | 60 | 838 | 94 | 10,65,25 |
| 9 | Triethylphosphite | 40 | 60 | 981 | 95 | 9,65,26 |
| 10 | Triisopropylphosphite | 40 | 60 | 1223 | 96 | 7,64,29 |
| 11 | Tri-n-butylphosphite | 40 | 60 | 2147 | 95 | 9,63,28 |
| 12 | Triphenylphosphite | 39 | 60 | 2366 | 94 | 8,65,27 |
| 13 | Tris(ortho-tolyl)phosphite | 40 | 30 | 4332 | 94 | 9,62,29 |
| 14 | Tricyclohexylphosphite | 40 | 60 | 1167 | 95 | 9,63,28 |

The results of Table II are similar to those of Table I, but indicate even higher productivities.

That which is claimed is:

1. A process for dimerizing ethylene to butenes comprising:
   (a) contacting ethylene, an organonickel(II) compound, a phosphite compound of the formula $P(OR)_3$ where R independently represents H or a $C_1$ to $C_{20}$ hydrocarbyl radical and where at least one R is not H, and an alkylaluminum compound having at least one $C_1$ to $C_{12}$ alkyl radical and at least one aluminum atom per molecule, wherein the ethylene is in a gaseous phase and the organonickel(II) compound, phosphite compound and alkylaluminum compound are in a solvent and in a liquid phase, thereby producing a precursor reaction mixture in a liquid phase;
   (b) contacting, after step (a), ethylene in a gaseous phase, the precursor reaction mixture, and a fluorinated organoacid in a liquid phase, thereby producing a product reaction mixture in a liquid phase comprising said butenes.

2. A process as recited in claim 1 wherein step (a) is carried out at a pressure of about 5 to about 5000 psig, at a temperature of about −100° C. to about 50° C., and for a time of about 1 minute to about 6 hours.

3. A process as recited in claim 2 wherein step (a) is carried out at a pressure of about 20 to about 1000 psig, at a temperature of about 15° C. to about 35° C., and for a time of about 15 minutes to about 3 hours.

4. A process as recited in claim 1 wherein step (b) is carried out at a pressure of about 5 to about 5000 psig, at a temperature of about 0° C. to about 125° C., and for a time of about 1 minute to about 15 hours.

5. A process as recited in claim 4 wherein step (b) is carried out at a pressure of about 200 to about 1000 psig, at a temperature of about 20° C. to about 50° C., and for a time of about 15 minutes to about 5 hours.

6. A process as recited in claim 1 wherein the fluorinated organoacid is contacted with ethylene prior to step (b).

7. A process as recited in claim 1 wherein the organonickel(II) compound is selected from the group consisting of bis(cyclopentadienyl) nickel(II), bis(pentamethylcyclopentadienyl) nickel(II), nickel(II) 2-ethylhexanoate, nickel(II) acetylacetonate, nickel(II) hexafluoroacetylacetonate and nickel(II) trifluoroacetylacetonate.

8. A process as recited in claim 7 wherein the organonickel(II) compound is nickel(II) acetylacetonate.

9. A process as recited in claim 1 wherein the phosphite compound is tris(ortho-tolyl)phosphite.

10. A process as recited in claim 1 wherein the alkylaluminum compound is a trialkylaluminum compound of the formula $AlR'_3$ where R' is said alkyl radical.

11. A process as recited in claim 10 wherein the alkyl aluminum compound is triethylaluminum.

12. A process as recited in claim 1 wherein the fluorinated organoacid is a fluorinated carboxylic acid of the formula R"COOH where R" represents a $C_1$ to $C_{10}$ hydrocarbyl radical having at least one fluorine (F) atom.

13. A process as recited in claim 12 wherein the fluorinated organoacid is trifluoroacetic acid.

14. A process as recited in claim 1 wherein the molar ratio of (i) the phosphite compound, (ii) the alkylaluminum compound, and (iii) the fluorinated organoacid, respectively, to the organonickel(II) compound are as follows: (i) about 0.1-5 to 1; (ii) about 1-10 to 1; and (iii) about 1-20 to 1.

15. A process as recited in claim 1 wherein the solvent is selected from the group consisting of: a saturated hydrocarbon or fluorinated hydrocarbon of the formula $C_nH_{2n+2-x}F_x$ where n=4, 5, 6, 7 or 8 and x=0, 1 or 2; and an aromatic hydrocarbon or fluorinated hydrocarbon of the formula $C_6H_{6-n}(R''')_n$, where n=0, 1, 2, 3 or 4 and R''' independently represents F or a $C_1$ to $C_6$ alkyl radical or fluorinated alkyl radical.

16. A process for dimerizing ethylene to butenes comprising:
(a) contacting ethylene, an organonickel(II) compound, a phosphite compound of the formula $P(OR)_3$ where R independently represents H or a $C_1$ to $C_{20}$ hydrocarbyl radical and where at least one R is not H, and an alkylaluminum compound having at least one $C_1$ to $C_{12}$ alkyl radical and at least one aluminum atom per molecule, wherein the ethylene is in a gaseous phase and the organonickel(II) compound, phosphite compound and alkylaluminum compound are in a solvent and in a liquid phase, and further wherein this step is carried out at a pressure of about 5 to about 5000 psig and at a temperature of about $-100°$ C. to about $50°$ C., thereby producing a precursor reaction mixture in a liquid phase;
(b) contacting, after step (a), ethylene in a gaseous phase, the precursor reaction mixture, and a fluorinated organoacid in a liquid phase, wherein this step is carried out at a pressure of about 5 to about 5000 psig and at a temperature of about $0°$ C. to about $125°$ C., thereby producing a product reaction mixture in a liquid phase comprising said butenes.

* * * * *